United States Patent [19]

Cox

[11] 4,439,428

[45] Mar. 27, 1984

[54] HERBICIDE

[75] Inventor: John M. Cox, Bracknell, England

[73] Assignee: Imperial Chemical Industries PLC, London, England

[21] Appl. No.: 434,227

[22] Filed: Oct. 14, 1982

[30] Foreign Application Priority Data

Nov. 2, 1981 [GB] United Kingdom ............... 8132982

[51] Int. Cl.$^3$ .......................... A01N 57/00; C07F 9/65
[52] U.S. Cl. .................................. 424/200; 424/199; 548/112
[58] Field of Search ........................ 548/112; 424/200

[56] References Cited

FOREIGN PATENT DOCUMENTS

2527676 1/1977 Fed. Rep. of Germany .
2924600 1/1981 Fed. Rep. of Germany .

OTHER PUBLICATIONS

Shishkin et al., Chemical Abstracts, vol. 86, (1977), 55529k.

*Primary Examiner*—Richard Raymond
*Attorney, Agent, or Firm*—Cushman, Darby & Cushman

[57] ABSTRACT

This invention relates to substituted phosphonic acid derivatives, and to their use as herbicides.

7 Claims, No Drawings

HERBICIDE

According to the present invention, there are provided phosphonic acid derivatives of the formula (I)

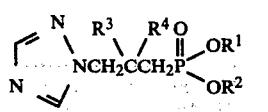 (I)

wherein $R^1$ and $R^2$ each represent hydrogen, a cation, or an optionally substituted aliphatic, alicyclic or phenyl radical; $R^3$ may be hydrogen or alkyl; $R^4$ may be hydrogen, hydroxy, fluoro, amino, optionally substituted alkoxy, alkenyloxy or alkynyloxy, optionally substituted alkylcarbonyloxy, optionally substituted benzoyloxy, carbamoyloxy, mono- or di-alkylcarbamoyloxy, optionally substituted benzyloxycarbonyloxy and phenoxycarbonyloxy, or alkoxycarbonyloxy; or $R^3$ and $R^4$ together with the carbon atom to which they are attached may represent a keto group, or a functional derivative thereof; or, in the case where neither of $R^1$ and $R^2$ is a cation an acid addition salt of a phosphonic acid derivative of formula (I). The term cation used above includes for example, alkali metal, alkaline earth metal, ammonium, organic ammonium, trialkylsulphonium, trialkylsulphoxonium, phosphonium, and amidinium cations. The term organic ammonium cation is intended to include ammonium cations prepared from low molecular weight amines, that is to say those having a molecular weight below about 300. Examples of such amines include alkylamines, alkenylamines, and alkanolamines containing not more than two amino groups, such as methylamine, ethylamine, n-propylamine, isopropyl-amine, n-butylamine, isobutylamine, sec-butylamine, n-amylamine, isoamylamine, dimethylamine, diethylamine, di n-propylamine, diisopropylamine, trimethylamine, triethylamine, tri-n-propylamine, triisopropylamine, tri-n-butylamine, ethanolamine, n-propanolamine, isopropanolamine, diethanolamine, dipropanolamine, N,N-diethylethanolamine, allylamine, methoxyethylamine, oleylamine, cyclohexylamine, tallowamine, ethylenediamine, propylene-diamine, aniline, o, m and p, methoxy-substituted aniline, o, m and p-toluidine and heterocyclic amines, for example pyridine, morpholine, piperidine and pyrrolidine.

Tetra-substituted ammonium cations are also included, for example tetra-methylammonium, tetrabutylammonium, and benzyltrimethylammonium cations.

Trialkylsulphonium cations include those, for example, in which each of the three alkyl groups, which are not necessarily all the same, may contain from 1 to 6 carbon atoms. Trialkylsulphoxonium cations likewise include those in which each of the three alkyl groups, which may be the same or different, may contain from 1 to 6 carbon atoms.

Phosphonium cations include, for example, cations in which the phosphorus atom bears four substituents, each of which may be an alkyl group of one to ten carbon atoms or a phenyl group, for example the tetramethylphosphonium, tetrabutylphosphonium, and tetraphenylphosphonium cations.

Amidinium cations include, for example, straight-chain amidinium cations of formula

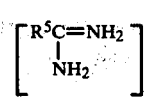

wherein $R^5$ is an alkyl radical of, for example, from 1 to 10 carbon atoms, and cyclic amidinium cations such as the protonated form of DBU, the formula of which is given at the end of Table 1 below. Alkali metal cations include lithium, sodium, and potassium; and alkaline earth metal cations include magnesium, calcium, strontium and barium.

When $R^1$ or $R^2$ is an aliphatic radical it may be, for example, an alkyl, alkenyl, or alkynyl radical. An alkyl radical may contain for example from 1 to 20 or more carbon atoms, and an alkenyl or alkynyl radical may contain from 3 to 20 or more carbon atoms. Examples of alkyl radicals include alkyl radicals of 1 to 6 carbon atoms, ie., methyl, ethyl, isopropyl, propyl, butyl, pentyl and hexyl. Examples of alkenyl and alkynyl radicals include such radicals containing from 3 to 6 carbon atoms, for example allyl, 2-butenyl, propargyl, and 2-butynyl radicals.

Examples of substituents which may be present in the alkyl, alkenyl or alkynyl radicals include hydroxy, alkoxy (eg. alkoxy of 1 to 6 carbon atoms), halogen (eg. chlorine) and phenyl (eg. $R^1$ or $R^2$ may be benzyl). When $R^1$ or $R^2$ is an alicyclic radical, it may be for example a cycloalkyl radical, eg. a cyclopentyl or cyclohexyl radical.

When $R^1$ or $R^2$ is an optionally substituted phenyl radical, examples of substituents which may be present include hydroxy, alkoxy of 1 to 6 carbon atoms, halogen (eg. fluorine, chlorine, or bromine) and alkyl of 1 to 4 carbon atoms.

When $R^3$ is an alkyl radical it may for example be an alkyl radical of 1 to 3 carbon atoms.

When $R^4$ is an optionally substituted alkoxy, alkenyloxy, or alkynyloxy radical, the alkoxy radical may contain, for example, from one to six carbon atoms, and the alkenyloxy and alkynyloxy radicals may contain from two to six carbon atoms. Examples of substituents which may be present in the alkoxy, alkenyloxy and alkynyloxy radicals include halogen (eg. fluorine or chlorine), alkoxy (eg. 1 to 6 carbon atoms), carboxy, alkoxycarbonyl and phenyl. When $R^4$ is an optionally substituted alkylcarbonyloxy radical, it may for example contain from 2 to 6 carbon atoms; it may be for example acetoxy, propionyloxy, or butyryloxy. Examples of substituents which may be present in the alkyl carbonyloxy radical include halogen (eg. fluorine or chlorine), phosphonomethylamino, and phenyl. Examples of substituted alkylcarbonyloxy radicals include chloroacetoxy, dichloroacetoxy, trichloroacetoxy, N-phosphonomethylglycyloxy

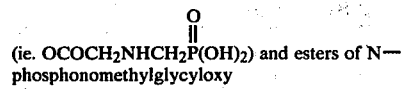

(ie. OCOCH₂NHCH₂P(OH)₂) and esters of N—phosphonomethylglycyloxy

(ie. OCOCH₂NHCH₂P(OR⁶)₂), where $R^6$ is alkyl of 1 to 6 carbon atoms.

When $R^4$ is an optionally substituted benzoyloxy radical, the substituents may include, for example, those recited above for the case when $R^1$ or $R^2$ is a substituted phenyl radical.

When $R^4$ is a mono- or di-alkyl carbamoyloxy radical, the alkyl group or groups may contain for example from 1 to 6 carbon atoms.

When $R^4$ is an optionally substituted benzyloxycarbonyloxy or phenoxycarbonyloxy radical, the substituents may include, for example, those recited above for the case when $R^1$ or $R^2$ is a substituted phenyl radical.

When $R^4$ is an alkoxycarbonyloxy radical it may contain, for example, from 2 to 6 carbon atoms; it may be for example a methoxycarbonyloxy or butoxycarbonyloxy radical.

When $R^3$ and $R^4$ together with the carbon atom to which they are attached comprise a keto group or a functional derivative thereof, the functional derivative may be any of the usual functional derivatives prepared from a ketone, for example an oxime, hydroazone, phenylhydrazone, semi-carbazone, or ketal.

Acid additions salts of compounds of the formula I include for example salts formed with mineral acids, for example the hydrochloride, sulphate, nitrate and phosphate.

Within the class of compounds defined above, one sub-class comprises compounds of formula (I) in which at least one of $R^1$ and $R^2$ is a cation which is an alkali metal, alkaline earth metal, ammonium, organic ammonium, trialkylsulphonium, trialkylsulphoxonium, phosphonium, or amidinium cation.

Within the foregoing sub-class, a further sub-class comprises compounds in which $R^3$ is hydrogen and $R^4$ is a hydroxy group.

Particular examples of compounds of the invention include those listed in Table I below.

TABLE 1

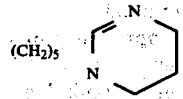

| Compound No | $R^1$ | $R^2$ | $R^3$ | $R^4$ |
|---|---|---|---|---|
| 1 | $C_2H_5$ | $C_2H_5$ | H | OH |
| 2 | H | H | H | OH |
| 3 | $C_2H_5$ | $C_2H_5$ | H | $OCOCH_3$ |
| 4 | H | H | H | $OCOCH_3$ |
| 5 | H | $C_2H_5$ | H | OH |
| 6 | $C_2H_5$ | iso $C_3H_7NH_3^+$ | H | OH |
| 7 | $C_2H_5$ | $C_2H_5$ | H | H |
| 8 | H | H | H | H |
| 9 | H | iso $C_3H_7NH_3^+$ | H | OH |
| 10 | $CH_3$ | $CH_3$ | | /O\ |
| 11 | H | H | | /O\ |
| 12 | $C_2H_5$ | $C_2H_5$ | H | $OCH_3$ |
| 12 | $C_2H_5$ | $C_2H_5$ | H | $OCH_3$ |
| 13 | H | H | H | $OCH_3$ |
| 14 | $C_2H_5$ | $C_2H_5$ | $CH_3$ | OH |
| 15 | H | $C_6H_5NH_3^+$ | $CH_3$ | OH |
| 16 | H | $(CH_3)_3S^+$ | H | OH |
| 17 | H | $(CH_3)_3SO^+$ | H | OH |
| 18 | $C_2H_5$ | $C_2H_5$ | iso $C_3H_7$ | OH |
| 19 | H | H | iso $C_3H_7$ | OH |
| 20 | H | H | | OH, —N— |

TABLE 1-continued

| Compound No | $R^1$ | $R^2$ | $R^3$ | $R^4$ |
|---|---|---|---|---|
| 21 | H | *DBUH+ | H | OH |
| 22 | DBUH+ | DBUH+ | H | OH |
| 23 | Hydrochloride of compound 2 | | | |

*DBU is an amine having the formula:

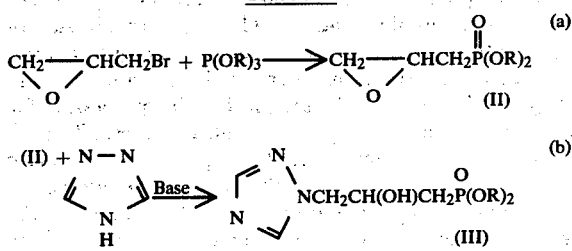

The compounds of the invention may be prepared by a variety of methods.

Compounds according to the invention wherein $R^3$ is H, $R^4$ is OH and $R^1$ and $R^2$ are aliphatic or phenyl radicals may be prepared by the process outlined in Scheme A below:

Scheme A (a) $CH_2\text{—}CHCH_2Br + P(OR)_3 \longrightarrow CH_2\text{—}CHCH_2P(OR)_2$ with epoxide O, giving (II) with $=O$ (b) (II) + N—N (triazole) $\xrightarrow{\text{Base}}$ NCH$_2$CH(OH)CH$_2$P(OR)$_2$ (III)

In Scheme A, R is an optionally substituted aliphatic or phenyl radical, for example a $C_{1-6}$ alkyl radical or a phenyl radical. In Step (a), epibromohydrin is heated with a trialkyl-phosphite or with triphenylphosphite to give the epoxide derivative (II). This is then reacted with 1,2,4-triazole in presence of a base to give the derivative (III).

The reaction may be carried out in a solvent inert towards the reactants, and may be accelerated by heating, for example to a temperature in the range from 50°–120° C. or more. The solvent may be, for example, methyl ethyl ketone. The base may be for example, an inorganic base eg. anhydrous potassium carbonate, sodium hydrogen carbonate, tetraalkylammonium halides or caesium fluoride. The product may be isolated by conventional methods, for example by separating the insoluble salts from the reaction mixture, evaporating the solvent under reduced pressure, and purifying the residue if required by known methods, for example by chromatography (eg. high performance liquid chromatography) and recrystallisation.

In a variation of Scheme A, trimethylsilyl-1,2,4-triazole may be reacted with the intermediate (II) to give the product of structure (IV) below, using caesium fluoride or tetrabutyl ammonium chloride as the base.

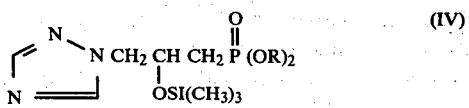

This may then be treated with a de-alkylating agent such as trimethylsilyl bromide followed by methanol, or hydrolysed with hydrochloric acid, as described for compound (III) above to give the product in which $R^1$ and $R^2$ are hydrogen. The trimethylsilyl ether group in formula (IV) is removed at the same time by these procedures to give the free hydroxy compound. Where the groups R in the compound of formula (IV) are optionally substituted phenyl, they are not removable by treatment with trimethylsilyl bromide and may be removed by acid hydrolysis.

Compounds in which $R^1$ and $R^2$ are hydrogen may be obtained by treating the derivative (III) with a dealkylating agent (eg. trimethyl silyl bromide followed by methanol), or by hydrolysis with a mineral acid (eg. hydrochloric acid). Compounds in which one of $R^1$ and $R^2$ is a hydrogen atom and the other is an alkyl group may be obtained by partial hydrolysis of the derivatives (III). Salts of compounds in which one or both of $R^1$ and $R^2$ is hydrogen may be prepared for example by partial or complete neutralisation of these acidic compounds with a metal hydroxide or carbonate, or with ammonia or an amine or by reaction with a trialkylsulphonium hydroxide, a trialkylsulphoxonium hydroxide, or a phosphonium hydroxide.

Compounds in which $R^3$ is alkyl may be prepared for example by the process of Scheme B:

Scheme B

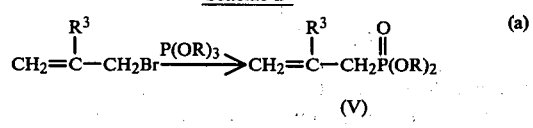

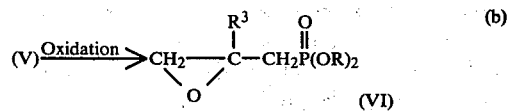

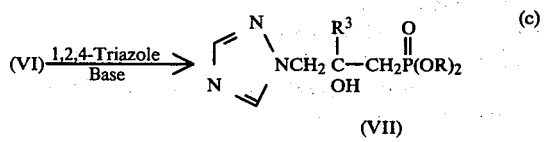

According to Scheme B, a suitably substituted allyl bromide is reacted with a tri-aliphatic or triphenyl phosphite to give (V). This is then oxidised by conventional methods to the epoxy compound (VI). Reaction with 1,2,4-triazole in presence of base as described in Scheme A above gives the triazole derivative (VII) which may if desired be converted to the corresponding compound in which R is hydrogen, by treatment with a de-alkylating agent or hydrolysis with a mineral acid as described in Scheme A.

Compounds in which $R^3$ and $R^4$ together with the carbon atom to which they are attached form a keto group may be prepared, for example, by the process of Scheme C.

Scheme C

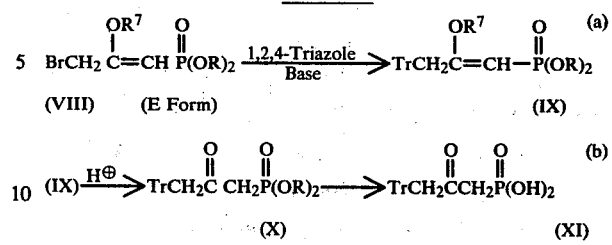

According to Scheme C, the phosphonate derivative (VIII) (in which $R^7$ stands for lower alkyl, eg. methyl or ethyl) is reacted with 1,2,4-triazole in presence of a base (eg. NaH) preferably in a solvent (eg. an ether, for example, tetrahydrofuran) to give the triazole derivative, (IX) (Tr stands for 1-(1,2,4-triazolyl)). The compound (IX) is then treated with acid (eg. by allowing it to stand with concentrated hydrochloric acid at room temperature) to give the ketone (X). If desired, the phosphorus ester groups R may be removed by reaction with a de-alkylating agent or by acid hydrolysis as described above for the corresponding step in Scheme A to give the ketone (XI). The ketone (XI) may be converted to a functional derivative if desired; for example the corresponding oxime may be prepared by reaction of (XI) with hydroxylamine. Alternatively the oxime may be prepared by reacting the phosphorus ester (X) directly with hydroxylamine, which simultaneously forms the oxime and removes the phosphorus ester groups.

The ketone (XI) may be converted into the corresponding hydroxy compound (III, R=H) by reduction, for example, by reduction with sodium borohydride, and this provides a method of preparing the latter compound further to that described in Scheme A.

Compounds in which $R^4$ is an alkoxy group or a substituted alkoxy group may be prepared, for example, by the process of Scheme D below:

Scheme D

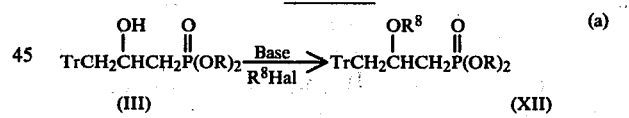

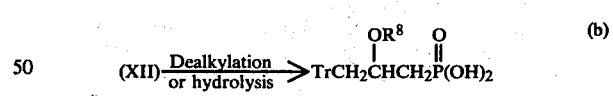

According to Scheme D, the phosphorus ester (III) is treated in the presence of a base with a halide $R^8$ Hal wherein Hal is chlorine, bromine, or iodine and $R^8$ is an optionally substituted alkyl, alkenyl, or alkynyl group. Conveniently, the base may be sodium hydride. The ether derivatives (XII) so obtained may then be converted to the corresponding phosphonic acid (XIII) by treatment with a de-alkylating agent or hydrolysis with a mineral acid as described above in the last step of Scheme A. Where the group $R^8$ contains an ester substituent (eg. ethoxy-carbonyl) this may be converted to the free carboxylic acid at this stage, and may require to be re-esterified by conventional procedures if the ester is required.

Compounds in which $R^4$ is an acyloxy group as hereinbefore defined may be prepared for example by acylating the phosphorus ester derivatives (III) as outlined in Scheme E below:

Scheme E

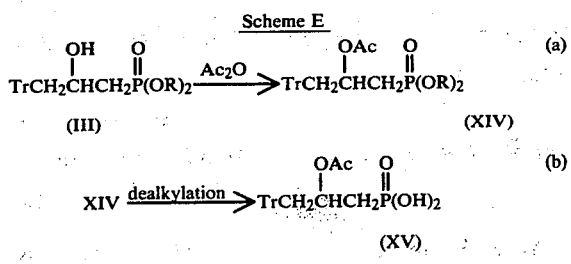

According to Scheme E, the phosphorus ester (III) is reacted with an acid anhydride Ac₂O to give the acyloxy derivative (XIV). This may then be converted to the corresponding phosphonic acid (XV) by reaction with a de-alkylating agent such as trimethylsilyl bromide as previously described for the last step of Scheme A.

The symbol AcO in the above Scheme corresponds to the values for alkylcarbonyloxy and optionally substituted benzoyloxy defined for R⁴ above.

In a variation of Scheme E, the phosphorus ester may be reacted with an acid chloride AcCl in presence of a base (eg. a tertiary amine, for example, pyridine or triethylamine) and preferably in a solvent (eg. dichloromethane). The group Ac in the acid chloride AcCl is defined as for the acyl group in the various acyloxy values defined above for the group R⁴ (ie. it may be acetyl, benzoyl, carbamoyl, benzyloxycarbonyl, etc).

In a further variation, where the appropriate carboxylic acid AcOH is conveniently available, the phosphorus ester (III) may be reacted with the acid AcOH in presence of dicyclohexylcarbo-diimide in presence of a base to give the ester (XIV). This procedure may be convenient for the preparation of compounds in which R⁴ is an N-phosphonomethylglycyloxy radical. These compounds may be obtained by reacting a protected form of N-phosphonomethylglycine, for example

(EtO)₂PCH₂N(COCF₃)CH₂CO₂H with the phosphorus ester (III) in presence of dicyclohexylcarbodiimide and a base, and then removing the protecting trifluoroacetyl group and the ester groups of the phosphonic acid moieties by standard procedures.

Compounds wherein R³ and R⁴ are both hydrogen may be prepared for example by the process of Scheme F.

Scheme F

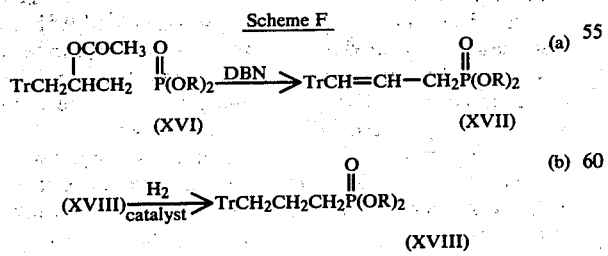

According to Scheme F, the acetoxy derivative (XVI) (prepared, for example, by the process outlined in Scheme E) is treated with 1,5-diazabicyclo[4.3.0]non-5-ene (DBN) or a similar strong amine base to bring about elimination of acetic acid, thereby forming the alkene derivative (XVIII). Preferably the reaction is carried out in a solvent (eg. acetonitrile). The reaction may be accelerated by heating (eg. to the reflux temperature of acetonitrile). The alkene (XVII) is then hydrogenated in presence of a noble metal catalyst (eg. 10% palladium on charcoal) to give the alkane derivative (XVIII). The phosphorus ester groups may then be removed by treatment with a de-alkylating agent as previously described. Alternatively, the phosphorus ester groups may be removed from the alkene (XVII), and the free phosphonic acid may be hydrogenated to give (XVIII).

Compounds of formula (I) in which one of the groups R¹ and R² is an aliphatic or phenyl radical and the other is hydrogen or a cation may be prepared by alkaline hydrolysis of compounds in which both R¹ and R² are aliphatic or phenyl groups.

Alkaline hydrolysis may be carried out by treating a compound of formula (I) in which both R¹ and R² are aliphatic or phenyl groups with aqueous sodium hydroxide. This gives rise to a compound in which one of the R¹ and R² groups is a sodium cation and the other remains as an aliphatic or phenyl group. This compound may be passed in aqueous solution through an ion exchange column in acid form to generate a compound of formula (I) in which one of the groups R¹ and R² is hydrogen and the other is aliphatic or phenyl.

Compounds according to the invention in which R³ is hydrogen and R⁴ is an —NH₂ group may be prepared, for example, by reductive amination as shown in Scheme G.

Scheme G

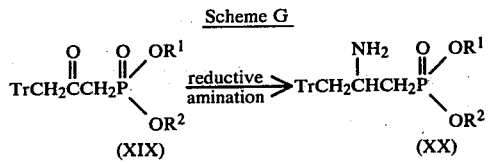

According to Scheme G, the ketone (XIX, R¹=R²=hydrogen, aliphatic or phenyl) is treated with a source of ammonia and a reducing agent, for example a combination of an ammonium salt (eg. ammonium acetate) with sodium cyanoborohydride, or the ketone (XIX) may be subjected to electrolytic reduction in presence of a mixture of ammonium chloride and ammonia solution.

Another possible procedure for preparing the amino compound (XX) is by reduction of the oxime derivative (XXI):

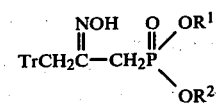

Another possible method for preparing the amino compound is outlined in Scheme H below:

Scheme H

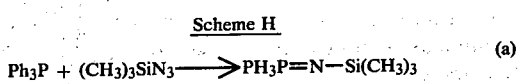

-continued
Scheme H

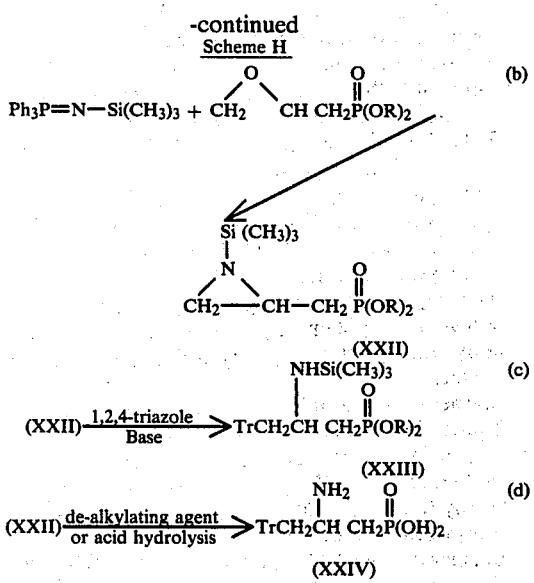

According to Scheme H, triphenylphosphine is heated with trimethylsilylazide to give a phosphine-imine derivative. This is then reacted in step (b) with the epoxypropylphosphonic acid derivative to give the intermediate (XXII). This in turn is reacted with 1,2,4-triazole in presence of a base to give the silylamino compound (XXIII). Treatment of this with a dealkylating agent, or acid hydrolysis as described above gives the amino compound (XXIV).

Compounds of the invention wherein $R^3$ is hydrogen and $R^4$ is fluorine may be prepared, for example, by the process outlined in Scheme I below:

Scheme I

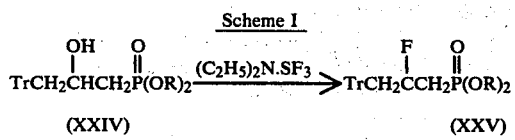

According to Scheme I, the hydroxy compound (XXIV, R as previously defined) is reacted with a fluorinating agent comprising diethylaminosulphur trifluoride, preferably in a solvent (eg. dichloromethane) to give the corresponding fluoro compound (XXV). If desired, this may then be treated with a de-alkylating agent or by acid hydrolysis as previously described to give the compound corresponding to XXV in which R stands for hydrogen.

The compounds of the invention are useful for controlling the growth of unwanted plants. According to another aspect of the invention, therefore, there is provided a process of killing unwanted plants, which comprises applying to the plants, or to the locus of the plants a herbicidal amount of a compound of formula (I) as hereinbefore defined. By the locus of the plants we mean the area of soil or other plant growth medium in which the plants are growing, or in which seeds of the unwanted plants are present. The rate at which the compound of formula (I) is applied to the plants or to the locus of the plants will depend upon a number of factors, for example the identity of the particular plant species to be controlled and the identity of the particular compound of formula (I) which is used, but in general an amount of from 0.2 to 10.0 kilograms per hectare may be employed. Within this range an amount of from 0.2 to 2 kilograms per hectare is often suitable. The skilled worker in the herbicidal art will be able to establish appropriate application rates by standard procedures without undue experimentation.

The compounds of the invention are herbicidally active against a wide range of mono- and di-cotyledonous plants including for example the sedges Cyperus esculentus and Cyperus rotundus, and the dicotyledonous perennial plant Convolvulus arvensis.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecyl-benzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many purposes contain between 0.01% and 10% and preferably between 0.1% and 1% by weight of the active ingredient.

It will be noted that many compounds of formula (I) above contain an asymmetric carbon atom, and in some cases more than one. As well known to those skilled in the art, compounds containing an asymmetric carbon atom are capable of existing in two optically isomeric forms (D and L forms). The present invention includes the separate D and L forms of the compounds as well as mixtures of the D and L forms in all proportions. Where the compound of the invention contains more than one asymmetic carbon atom, the invention includes the separate diastereoisomers and their mixtures in all proportions. As prepared by chemical synthesis, compounds containing an asymmetric carbon atom are usually obtained as mixtures of equal proportions of the D and L forms (racemic mixtures). Methods of separating racemic mixtures into the D and L forms are well known in the art.

The compounds of the invention can be used in association (for example in the form of a mixture) with another herbicide.

Examples of such herbicides are:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (eg. salts, esters and amides);

C. 3-[4-(4-halophenoxy)phenyl]-1,1-dialkylureas such as 3-[4-(4-chlorophenoxy)phenyl]-1,1-dimethylurea (chloroxuron);

D. dinitrophenols and their derivatives (eg. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxycarbonylamino]phenyl (3-methylphenyl)-carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron).

L. thiolcarbamate herbicides such as S-propyl dipropylthiocarbamate (verolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl- -chloro-2',6'-diethylacetanilide (butachlor), the corresponding N-methoxy compound (alachlor), the corresponding N-i-propyl compound (propachlor) and 3',4'-dichloropropionanilide (propanil);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil).

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid, 2-chloro-4-trifluoromethylphenyl 3-ethoxy-4-nitrophenol ether and the compounds of European Patent Specification Publication No. 3416 (the disclosure of which Specification is incorporated herein by reference); and S. miscellaneous herbicides including N,N-dimethyldiphenylacetamide (diphenamid), N-(1-naphthyl)-phthalamic acid (naptalam) 3-amino-1,2,4-triazole, phosphinothricin (ie. 2-amino-4-methylphosphino butyric acid) and salts thereof, and N-phosphonomethylglycine and salts thereof.

T. bipyridylium herbicides such as those in which the active entity is the 1,1'-dimethyl-4,4'-dipyridylium ion (paraquat) and those in which the active entity is the 1,1'-ethylene-2,2'dipyridylium ion (diquat).

U. Aryloxyphenoxypropionic acids and their derivatives (salts, esters, amides, and the like).

Examples of such acids are:

2-[4-(5-trifluoromethylpyridyl-2-oxy)phenoxy]propionic acid.

2-[4-(4-trifluoromethylphenoxy)phenoxy]propionic acid.

2-[4-(2,4-dichlorophenoxy)phenoxy]propionic acid.

2-[4-(6-chlorobenzoxazolyl-2-oxy)phenoxy]propionic acid 4-methyl-4-(4-trifluoromethylphenoxy)phenoxybut-2-enoic acid.

V. Cyclohexenone herbicides, for example alloxydim-sodium (NP48) and sethoxydim (NP55).

The amount of the other herbicide to be used in association with a compound of the invention may vary, depending upon the particular weed population to be controlled, but in general one part of a compound of the invention will be used with from 0.1 to 10.0 parts of the other herbicide.

The invention is illustrated by the following Examples, in which unless otherwise stated, all parts are by weight and all temperatures are in degrees Celsius.

EXAMPLE 1

This Example illustrates the preparation of diethyl 2-hydroxy-3(1,2,4-triazol-1-yl)propylphosphonate (Compound No. 1 of Table 1).

A mixture of diethyl 2,3-epoxypropylphosphonate (14.55 g), 1,2,4-triazole (5.18 g), potassium carbonate (10.35 g) and methyl ethyl ketone (220 ml) was heated under reflux for four hours. The supernatant liquid was decanted from a sticky residue and evaporated under reduced pressure. The crude product was purified by preparative high performance liquid chromatography (using a Waters LC 500 apparatus, silica as solid phase, and ethanol: ether in the proportion of 1:2 by volume as the liquid phase) to give diethyl 2-hydroxy-3(1,2,4-triazol-1-yl)propylphosphonate (7.5 g) as a pale yellow viscous oil. The identity of the product was confirmed by examination of its infra-red; mass; and proton, $P^{31}$ and $C^{13}$ nuclear magnetic resonance spectra, which were all consistent with the structure assigned.

Other combinations of basic catalysts, and solvents, eg. sodium bicarbonate in eg. methyl ethyl ketone; caesium fluoride or quaternary ammonium halides used eg. without solvent can be employed. The latter bases can also be used in conjunction with N-trimethylsilyltriazole in place of triazole itself. The resulting silyl ether can be cleaved during the conversion of the phosphonic ester to phosphonic acid as described in Examples Nos. 2 and 3.

EXAMPLE 2

This Example illustrates the preparation of 2-hydroxy-3-(1,2,4-triazol-1-yl)propylphosphonic acid (Compound No. 2 of Table I).

Trimethylsilyl bromide (6.0 ml) was added to a solution of diethyl 2-hydroxy-3-(1,2,4-triazol-1-yl)propylphosphonate (2.0 g, prepared as described in Example 1) in dichloromethane (40 ml). The mixture was allowed to stand for eighteen hours at 20° C., evaporated under reduced pressure, treated with methanol (5 ml) and again evaporated. The residue was dissolved in a mixture of methanol and ether and the solution treated dropwise with aniline until a sticky white solid separated. This was triturated with ether, then with a small volume of methanol and finally with acetone to give, after drying, the required phosphonic acid (0.9 g) as a white solid, m.p. 162°–165° C. The spectral characteristics of this product were in agreement with those expected for the structure assigned. The elemental analysis figures were as follows:

$C_5H_{10}N_3O_4P$ required: C, 28.99; H, 4.87; N, 20.29 found: C, 28.48; H, 4.72; N, 19.98%

EXAMPLE 3

This Example illustrates the preparations of 2-hydroxy-3-(1,2,4-triazol-1-yl)propylphosphonic acid hydrochloride (Compound No. 23 of Table I) and thence the free base (Compound No. 2 of Table I).

A mixture of diethyl 2-hydroxy-3-(1,2,4-triazol-1-yl)propylphosphonate (50.0 g, prepared as described in Example 1) and concentrated hydrochloric acid (300 ml) was heated under reflux for three hours, evaporated under reduced pressure, finally at 0.01 mm, to give a brown viscous oil. This was treated with methanol (100 ml) and the mixture allowed to stand. The off-white crystalline solid was filtered, washed with methanol and dried to give Compound No. 23 of Table I (29.0 g, m.p. 165°–168° C.). The elemental analysis figures were as follows:

$C_5H_{11}ClN_3O_4P$ requires: C, 24.65; H, 4.55; N, 17.25 found: C, 24.50; H, 4.32; N, 17.18%

Compound No. 23 of Table I was dissolved in water, treated with an equimolar quantity of sodium hydroxide dissolved in water, evaporated to dryness and extracted with methanol. The extract was evaporated to dryness to give an essentially quantitative recovery of Compound No. 2 of Table I, contaminated by small amounts of sodium chloride. Salt content can be reduced by repeating the extraction procedure.

EXAMPLE 4

This Example illustrates the preparation of amine and amidine salts of 2-hydroxy-3-(1,2,4-triazol-1-yl)propylphosphonic acid (Compound Nos. 9, 21 and 22 of Table I).

Isopropylamine (0.24 g) was added dropwise to a suspension of Compound No. 2 of Table I (0.80 g, prepared as described in Example 2) in methanol (5 ml). The solution was allowed to stand for thirty minutes at 20° C. and evaporated under reduced pressure. The residue was triturated with a mixture of methanol and ether, filtered and dried to give Compound No. 9 of Table I (660 mg, m.p. 163°–165° C.). The proton magnetic resonance spectrum was consistent with the material being the monoisopropylamine salt.

Mono- and bis- DBU (1,8-Diazabicyclo[5.4.0]undec-7-ene) salts were made similarly by the addition of one or two equivalents, respectively, of the base to an aqueous solution of the acid. Evaporation and trituration with ether gave Compound Nos. 21 and 22 of Table I. The ratio of acid to base was again established by proton magnetic resonance spectroscopy.

EXAMPLE 5

This Example illustrates the preparation of sulph(ox)onium salts of 2-hydroxy-3-(1,2,4-triazol-1-yl)propylphosphonic acid (Compound Nos. 16 and 17 of Table I).

A solution of trimethyl sulphonium hydroxide, generated by passing an aqueous solution of the corresponding iodide (1.60 g) through a column of Amberlyst A-26 ion-exchange resin, was treated with a solution of the free acid (2.07 g, prepared as described in Example 2) in water (30 ml). The mixture was evaporated under reduced pressure to give a colourless glass, the proton magnetic resonance spectrum of which suggested a purity of >90% with respect to Compound No. 16 of Table I.

The trimethylsulphoxonium salt (Compound No. 17 of Table I) was made similarly with the difference that it was necessary to use a dimethyl sulphoxide and water mixture for the chromatographic generation of the sulphoxonium hydroxide. The crude salt was triturated with chloroform to give material m.p. 85° C. (decomp) of >90% purity.

EXAMPLE 6

This Example illustrates the preparation of ethyl 2-hydroxy-3-(1,2,4-triazol-1-yl)propylphosphonate and its isopropylamine salt (Compound Nos. 5 and 6 of Table I).

A mixture of diethyl 2-hydroxy-3-(1,2,4-triazol-1-yl)propylphosphonate (2.9 g, prepared as described in Example 1) and M sodium hydroxide solution (11.0 ml) was heated under reflux for two hours, then evaporated under reduced pressure. An aqueous solution of the residue was passed through a column of Dowex 50W-X8 (H+) ion-exchange resin to give, after evaporation under reduced pressure, a pale yellow glass (2.1 g) of Compound No. 5 of Table I.

Isopropylamine (0.29 g) was added to a solution of Compound 5 of Table I (1.06 g) in ethanol (10 ml). Dilution with ether gave a white solid which has filtered off, washed several times with ether and dried to give Compound No. 6 of Table I (1.25 g, m.p. 139°–141° C.).

EXAMPLE 7

This Example illustrates the preparation of dimethyl 2-oxo-3-(1,2,4-triazol-1-yl)propylphosphonate (Compound No. 10 of Table I).

A solution of 1,2,4-triazole (10.67 g) in dry tetrahydrofuran (THF, 300 ml) was added dropwise to a stirred suspension of sodium hydride (7.56 g, 50% suspension in mineral oil, prewashed with petroleum, b.p. 40°–60° C.) in dry THF (50 ml) maintained at a temperature of less than 20° C. The mixture was stirred for forty-five minutes at 20° C., then treated dropwise over thirty-five minutes with a solution of E-dimethyl 3-bromo-2-ethoxyprop-1-enyl phosphonate (42.17 g, prepared as described in Canadian J. Chem., 1982, 60, 1114) in dry THF (60 ml). It was then heated under reflux for ninety minutes, cooled, concentrated to one-quarter bulk, treated with saturated aqueous sodium bicarbonate solution and extracted several times with ethyl acetate. The extracts were washed with a little brine, dried over magnesium sulphate and evaporated to give E-dimethyl 2-ethoxy-3-(1,2,4-triazol-1-yl)prop-1-enyl phosphonate (32.91 g).

This material (10.0 g) was dissolved with stirring in concentrated hydrochloric acid (25 ml). After fifteen minutes sodium bicarbonate was added until the paste remaining had pH >7. The paste was extracted with ethyl acetate (8×100 ml) and the extracts dried over magnesium sulphate and evaporated under reduced pressure. The residue was purified by chromatography on silica using ethanol as eluant to give Compound No. 10 of Table I (5.70 g), identified by proton magnetic resonance spectroscopy and mass spectrometry.

EXAMPLE 8

This Example illustrates the preparation of 2-oxo-3-(1,2,4-triazol-1-yl)propylphosphonic acid (Compound No. 11 of Table I) and its reduction to the corresponding alcohol (Compound No 2 of Table I).

A mixture of dimethyl 2-oxo-3-(1,2,4-triazol-1-yl)propylphosphonate (1.0 g, prepared as described in Example 7), trimethylsilyl bromide (2.0 ml) and dichloromethane (10 ml) was allowed to stand overnight at 20° C., then evaporated under reduced pressure. The residue was dissolved in methanol (8 ml) and the solution again evaporated under reduced pressure. The crude product was dissolved in methanol and treated with ether, then aniline, until trituration produced a solid precipitate. Ths was washed with ether and dried to give Compound No. 11 of Table I (0.72 g, m.p. 153°–157° C.).

Sodium borohydride (80 mg) was added portionwise to a refluxing mixture of Compound No. 11 of Table I (100 ml) and methanol (2.0 ml) over a period of one hour. The mixture was treated with 1 M hydrochloric acid, evaporated under reduced pressure and the residue chromatographed in water on a column of Dowex 50W-X8 (H+) resin. Appropriate fractions were shown, by analytical HPLC on a Spherisorb S5NH weak base ion-exchange resin and fast-atom bombardment mass spectrometry, to contain Compound No. 2 of Table I contaminated with a small proportion of Compound No. 11 of Table I.

EXAMPLE 9

This Example illustrates the preparation of diethyl 2-acetoxy-3-(1,2,4-triazol-1-yl)propylphosphonate and the corresponding phosphonic acid (Compound Nos. 3 and 4 of Table I, respectively).

A mixture of diethyl 2-hydroxy-3-(1,2,4-triazol-1-yl)propylphosphonate (2.5 g, prepared as described in Example 1) and acetic anhydride (15 ml) was heated at 90° C. for three hours, then distilled to give Compound No. 3 of Table I (1.57 g, pale yellow viscous oil, b.p. 114°–118°/0.03 mm).

This material (1.0 g) was treated with trimethylsilyl bromide in a manner similar to that described in Example 2 to give an off-white gum. Trituration with acetone gave Compound No. 4 of Table I (0.505 g, white glass) identified by proton magnetic resonance spectroscopy and mass spectrometry.

EXAMPLE 10

This Example illustrates the preparation of diethyl 2-methoxy-3-(1,2,4-triazol-1-yl)propylphosphonate and the corresponding phosphonic acid (Compound Nos. 12 and 13 of Table I, respectively).

A solution of diethyl 2-hydroxy-3-(1,2,4-triazol-1-yl)propylphosphonate (2.60 g, prepared as described in Example 1) in dry tetrahydrofuran (THF, 15 ml) was added dropwise with stirring to a suspension of sodium hydride (0.50 g, 50% suspension in mineral oil, prewashed with petroleum b.p. 60°–80° C.) in dry THF, maintaining a temperature of less than 20° C. The mixture was stirred for one hour at room temperature, treated with methyl iodide (5.0 ml) and stirred for a further one hour. It was then filtered and evaporated under reduced pressure. The residue was treated with chloroform, filtered and the filtrate evaporated to give Compound No. 12 of Table I (1.62 g).

This material (1.40 g) was treated with trimethylsilyl bromide in a manner similar to that described in Example 2 to give Compound No. 13 of Table I as a sticky white solid (0.45 g), identified by proton magnetic resonance spectroscopy and mass spectrometry.

EXAMPLE 11

This Example illustrates the preparation of diethyl 3-(1,2,4-triazol-1-yl)propyl phosphonate and the corresponding phosphonic acid (Compound Nos. 7 and 8 of Table I, respectively).

A mixture of diethyl 2-acetoxy-3-(1,2,4-triazol-1-yl)propylphosphonate (13.20 g, prepared as described in Example 9), 1,5-diazabicyclo[4.3.0]non-5-ene (5.50 g) and acetonitrile (100 ml) was heated under reflux for twenty hours then evaporated under reduced pressure. The residue was dissolved in water (50 ml), brought to pH5 with concentrated hydrochloric acid and extracted with ethyl acetate (3×100 ml). The extracts were washed with brine, dried over magnesium sulphate and evaporated under reduced pressure to give E-diethyl 3-(1,2,4-triazol-1-yl)prop-2-enyl phosphonate (7.42 g) as a yellow oil.

This material (2.0 g) was hydrogenated in methanol (30 ml) over 10% palladium on carbon (100 mg) at atmospheric pressure and 20° C. The mixture was filtered through 'Supercel' and evaporated to give Compound No. 7 of Table I (2.01 g) as a pale yellow oil identified by proton magnetic resonance spectroscopy and mass spectrometry.

This material (1.2 g) was treated with trimethylsilyl bromide in a manner similar to that described in Example 2 to give a viscous brown oil. Trituration with a mixture of isopropanol and ether, then isopropanol alone gave Compound No. 8 of Table I (0.43 g, white solid, m.p. 144°–146° C.).

EXAMPLE 12

This Example illustrates the preparation of 2-oximino-3-(1,2,4-triazol-1-yl)propylphosphonic acid (Compound No. 20 of Table I).

Hydroxylamine hydrochloride (2.1 g) was added to a stirred solution of 2-oxo-3-(1,2,4-triazol-1-yl)propyl phosphonic acid (3.1 g) in water (80 ml) and methanol (20 ml). After two hours, the mixture was evaporated under reduced pressure and chromatographed in water on a column of Amberlite CG 120 (H+) ion-exchange resin. Those fractions containing the desired product, contaminated with the ketonic starting material, were combined, evaporated under reduced pressure and chromatographed using HPLC on a column containing 12% propylamino-bonded silica gel and 0.1 M potassium dihydrogen phosphate as eluant. Fractions containing pure oxime were combined and evaporated under reduced pressure. The residue was extracted with methanol, filtered and the extracts evaporated under reduced pressure to give a white solid [0.94 g, m.p. 80° (decomp)] containing Compound No. 20 of Table I and potassium dihydrogen phosphate in a ratio of 7:3.

EXAMPLE 13

This Example illustrates the preparation of diethyl 2-hydroxy-2-methyl-3-(1,2,4-triazol-1-yl)propylphosphonate and the anilinium salt of the corresponding phosphonic acid (Compound Nos. 14 and 15 of Table I, respectively).

A mixture of methallyl bromide (15.4 g) and triethyl phosphite (60 ml) was heated under reflux for six hours, then fractionally distilled to give diethyl-2-methylenepropyl phosphonate (18.56 g, b.p. 95°–100° C./14 mm).

A solution of this material (9.44 g) in dichloromethane (65 ml) was added dropwise to a stirred solution of 3-chloroperbenzoic acid (9.7 g) in dichloromethane (65 ml) maintained at 10° C. The reaction mixture was allowed to stand for twenty hours at 20° C., diluted with dichloromethane (150 ml), washed with saturated aqueous sodium bicarbonate solution and water. After drying over magnesium sulphate, it was evaporated under reduced pressure, finally at 0.01 mm, to give the appropriate epoxide (10.85 g).

A flask containing a mixture of this material (9.52 g), 1,2,4-triazole (4.80 g) and caesium fluoride (1.0 g) was immersed in an oil-bath at 100° C. The temperature was raised to 120° C. and stirring continued for fifteen minutes. The reaction mixture was cooled and diluted with ethyl acetate (100 ml) and water (2 ml). The organic phase was dried over magnesium sulphate and evaporated under reduced pressure, finally at 120° C./0.1 mm. The residue (11.95 g) was purified by HPLC on silica using a mixture of ether and ethanol in a ratio of 2:1 by volume as eluant to give Compound No. 14 of Table I (2.30 g) as a yellow viscous oil.

This material (1.50 g) was treated with trimethylsilyl bromide in a manner similar to that described in Example 2. The crude product was triturated with isopropanol to give a white solid (0.63 g, m.p. 187°–189° C.) shown, by proton magnetic resonance spectroscopy to be Compound No. 15 of Table I, ie. the monoanilinium salt of the desired phosphonic acid.

EXAMPLE 14

This Example illustrates the preparation of diethyl 2-hydroxy-2-isopropyl-3-(1,2,4-triazol-1-yl)propylphosphonate and the corresponding phosphonic acid (Compound Nos. 18 and 19 of Table I, respectively).

A mixture of 2-methyl-2-methylenebutyl bromide (10.91 g), prepared as described in J. Chem. Soc. (c), 1971, 1968, and triethylphosphite (45 ml) was heated under reflux for five hours, cooled and fractionally distilled to give diethyl 3-methyl-2-methylenebutylphosphonate (12.54 g, b.p. 111°–116° C./14 mm).

This material (12.54 g) was oxidised with 3-chloroperbenzoic acid in a manner similar to that described in Example 13 to give the corresponding epoxide (12.85 g).

A flask containing a mixture of this material (12.85 g), 1,2,4-triazole (5.7 g) and caesium fluoride (1.0 g) was immersed in an oil bath at 90° C. The temperature was raised to 120° C. and stirring continued for thirty minutes. The reaction mixture was allowed to cool and diluted with ethyl acetate (100 ml) and water (3 ml). The organic phase was dried over magnesium sulphate and evaporated under reduced pressure, finally at 120°/0.2 mm. The residue (16.52 g) was purified by HPLC on silica using a mixture of ether and ethanol in a ratio of 4:1 by volume as eluant to give Compound No. 18 of Table I (3.0 g) contaminated with a little 1,2,4-triazole.

A mixture of this material (2.4 g), trimethylsilyl bromide (7.2 ml) and dichloromethane (50 ml) was allowed to stand at 20° C. for twenty hours, filtered and evaporated under reduced pressure. The residue was dissolved in methanol and the solution again evaporated, finally at 0.005 mm, to give Compound No. 19 of Table I (1.95 g) as a pale orange viscous liquid. The structure was established by proton magnetic resonance spectroscopy and fast-atom bombardment mass spectrometry.

EXAMPLE 15

This Example illustrates the herbicidal properties of compounds of the invention. The compounds were formulated for test by mixing an appropriate amount with 0.7 ml of a solution of a mixture of "Tween" 85 and Synperonic NPE 1800 in cyclohexanone. "Tween" 85 is a Trade Mark for condensate of sorbitan trioleate with 20 molar proportions of ethylene oxide. Synperonic NPE 1800 is a Trade Mark for a condensate of p-nonylphenol with propylene oxide and ethylene oxide. The concentration of the "Tween"/"Synperonic" mixture was 5 grams per 100 ml of cyclohexanone and the ratio of "Tween" to "Synperonic" in the mixture was 1:2. The mixture of the compound and the cyclohexanone solution was shaken with glass beads and diluted to 7 ml with water.

The spray composition so prepared was sprayed on to young pot plants (post-emergence test) of the species named in Table 2 below, at a rate equivalent to 1000 liters per hectare. Damage to plants was assessed by comparison with untreated plants, on a scale of 0 to 3 where 0 is no effect and 3 represents 75 to 100% kill. The interval in days between spraying and assessment is indicated in the table by the figure in brackets in the column headed "Pre- or Post-Emergence Application". In a test for pre-emergence herbicidal activity, seeds of the test species were placed on the surface of plastic trays of soil and were sprayed with the compositions, prepared again as above, at the rate of 1000 liters per hectare. The seeds were then covered with further soil. Three weeks after spraying, the seedlings in the sprayed plastic trays were compared with the seedlings in unsprayed control sprays, the damage being assessed on the same scale of 0 to 3. The results are given in Table 2 below:

TABLE 2

| COMPOUND NO | RATE OF APPLICATION kg/ha | PRE- OR POST-EMERGENCE APPLICATION | TEST PLANTS | | | | | |
|---|---|---|---|---|---|---|---|---|
| | | | Lt | To | Av | St | Ll | Cn |
| 1 | 10 | Pre (28) | 0 | 0 | 1 | 0 | 0 | 0 |
| | | Post (21) | 0 | 2 | 3 | 3 | 1 | 1 |
| 3 | 10 | Pre (20) | 0 | 0 | 0 | 0 | 1 | 0 |
| | | Post (13) | 0 | 0 | 0 | 3 | 0 | 0 |
| 4 | 5 | Pre (20) | 2 | 2 | 0 | 3 | 2 | — |
| | | Post (21) | 3 | — | 3 | 3 | 2 | 2 |
| 4 | 1 | Pre (20) | 0 | 0 | 0 | 0 | 0 | 1 |
| | | Post (21) | 3 | 3 | 3 | 3 | 3 | 1 |
| 7 | 5 | Pre (20) | 1 | 1 | 0 | 0 | 0 | 0 |
| | | Post (13) | 0 | 0 | 0 | — | 0 | 0 |
| 10 | 10 | Pre (20) | 0 | 0 | 1 | 0 | 1 | 0 |
| | | Post (13) | 0 | 0 | 0 | 0 | 0 | 0 |

The names of the test plants in Table 2 are as follows:

| Lt | Lettuce |
|---|---|
| To | Tomato |
| Av | Avena fatua |
| St | Setaria viridis |
| Ll | Perennial rye-grass (Lolium perenne) |
| Cn | Cyperus rotundus |

EXAMPLE 16

This Example illustrates the herbicidal properties of compounds of the invention. The Compounds were submitted to herbicide tests as described below.

Each compound was formulated for test by mixing an appropriate amount of it with 1.8 ml of a solution containing 10 grams per 100 ml of a mixture of equal parts by weight of Span 80 and Tween 20 in methylcyclohexanone. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the methylcyclohexanone solution was then shaken with glass beads and diluted to 45 ml with water. The spray compositions so prepared was sprayed on to young pot plants (post-emergence test) of the species named in the Table below, at a rate equivalent to 1000 liters per hectare. Damage to plants was assessed by comparison with untreated plants, on a scale of 0 to 5 where 0 is 0 to 20% damage and 5 is complete kill. In the Table of results, a dash (—) means that no test was made, and the figures in brackets in the column headed "Pre- or Post-Emergence Application" indicate the number of days elapsed between spraying and assessment of damage.

A test was also carried out to detect pre-emergence herbicidal activity. Seeds of the test species were placed on the surface of plastic trays of soil and were sprayed with the compositions at the rate of 1000 liters per hectare. The seeds were then covered with further soil. Seventeen days after spraying, the seedlings in the sprayed plastic trays were compared with the seedlings in unsprayed control trays, the damage being assessed on the same scale of 0 to 5.

The results of the tests are given in Table 3 below.

TABLE 3

| COMPOUND NO | RATE OF APPLICATION kg/ha | PRE- OR POST-EMERGENCE APPLICATION | TEST PLANTS | | | | | | | | | | |
|---|---|---|---|---|---|---|---|---|---|---|---|---|---|
| | | | Sb | Rp | Ct | Sy | Mz | Ww | Rc | Sn | Ip | Am | Pi | Ca |
| 2 | 2 | Pre (28) | 1 | 0 | 1 | 1 | 0 | 0 | 0 | 1 | 1 | 0 | — | 0 |
| | | Post (28) | 5 | 5 | 4 | 3 | 4 | 4 | 4 | 5 | 5 | 5 | — | 5 |
| 2 | 1 | Post (28) | 4 | 4 | 3 | 3 | 5 | 4 | 4 | 4 | 5 | 4 | — | 4 |
| 2 | 0.5 | Post (28) | 3 | 3 | 0 | 2 | 3 | 3 | 3 | 4 | 2 | 4 | — | 4 |
| 5 | 5 | Pre (20) | 3 | 1 | 1 | 2 | 3 | 4 | 4 | 3 | 4 | 1 | 3 | 3 |
| | | post (21) | 3 | 1 | 1 | 3 | 3 | 4 | 4 | 3 | 3 | 1 | 3 | 1 |
| 5 | 1 | Pre (20) | 2 | 0 | 1 | 1 | 1 | 2 | 2 | 2 | 2 | 0 | 1 | 1 |
| | | Post (21) | 0 | 0 | 1 | 1 | 3 | 2 | 3 | 3 | 3 | 1 | 0 | 0 |

TABLE 2-continued

| COMPOUND NO | RATE OF APPLICATION kg/ha | PRE- OR POST-EMERGENCE APPLICATION | TEST PLANTS | | | | | |
|---|---|---|---|---|---|---|---|---|
| | | | Lt | To | Av | St | Ll | Cn |
| | | Post (13) | 0 | 0 | 0 | 0 | 0 | 0 |

TABLE 3-continued

| | | | | | | | | | | | | | | |
|---|---|---|---|---|---|---|---|---|---|---|---|---|---|---|
| 6 | 5 | Pre (28) | 3 | 1 | 1 | 2 | 2 | 2 | 2 | 2 | 2 | 0 | 2 | — |
| | | Post (13) | 2 | 2 | 0 | 2 | 3 | 4 | 4 | 3 | 1 | 3 | 2 | 3 |
| 8 | 5 | Post (21) | 2 | 3 | 1 | 0 | 3 | 4 | 2 | 2 | 2 | 1 | 2 | 1 |
| 9 | 4 | Pre (20) | 2 | 0 | 0 | 0 | 2 | 2 | 2 | 2 | 2 | 1 | 3 | 2 |
| 9 | 2 | Post (21) | 4 | 2 | 2 | 3 | 3 | 4 | 3 | 4 | 4 | 3 | 4 | — |
| 9 | 1 | Post (21) | 3 | 2 | 1 | 2 | 4 | 4 | 3 | 4 | 3 | 3 | 4 | — |
| 9 | 0.5 | Post (21) | 2 | 2 | 1 | 2 | 4 | 3 | 3 | 4 | 3 | 1 | 2 | — |
| 13 | 5 | Pre (20) | 0 | 0 | 0 | 0 | 0 | 0 | 0 | 2 | 0 | 3 | 3 | — |
| | | Post (13) | 1 | 2 | 2 | 2 | 3 | 2 | 2 | 3 | 3 | 2 | 2 | — |
| 15 | 5 | Pre (20) | 0 | 0 | 0 | 0 | 0 | 0 | 0 | 0 | 0 | 0 | 0 | — |
| | | Post (13) | 2 | 0 | 0 | 1 | 3 | 4 | 4 | 4 | 2 | 2 | 3 | — |
| 16 | 2 | Post (21) | 3 | 3 | 2 | 4 | 4 | 4 | 4 | 4 | 4 | 3 | 3 | — |
| 17 | 1 | Post (21) | 3 | 2 | 3 | 3 | 4 | 4 | 4 | 3 | 3 | 2 | 3 | — |
| 23 | 1 | Post | 5 | 5 | 3 | 3 | 4 | 4 | 4 | 4 | 5 | — | — | 5 |

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Ga | Xa | Ab | Co | Av | Dg | Al | St | Ec | Sh | Ag | Cn |
| 2 | 2 | Pre (28) | 0 | 0 | 0 | 2 | 0 | 0 | 1 | 1 | 0 | 2 | 5 | 2 |
| | | Post (28) | 4 | 5 | 5 | 4 | 4 | 5 | 4 | 5 | 5 | 5 | 3 | 4 |
| 2 | 1 | Post (28) | 4 | 5 | 5 | 4 | 3 | 5 | 4 | 5 | 4 | 5 | 4 | 4 |
| 2 | 0.5 | Post (28) | 4 | 4 | 5 | 4 | 2 | 5 | 3 | 5 | 4 | 4 | 4 | 3 |
| 5 | 5 | Pre (20) | 3 | 1 | 2 | 1 | 3 | 3 | 3 | 4 | 3 | 3 | 5 | 5 |
| | | post (21) | 4 | 2 | 4 | 4 | 4 | 4 | 4 | 4 | 4 | 4 | 3 | 3 |
| 5 | 1 | Pre (20) | 1 | 0 | 0 | 1 | 1 | 3 | 2 | 3 | 1 | 2 | 5 | 3 |
| | | Post (21) | 2 | 1 | 3 | 3 | 2 | 3 | 3 | 4 | 3 | 3 | 3 | 1 |
| 6 | 5 | Pre (28) | 1 | 0 | 2 | 1 | 0 | 3 | 1 | 4 | 1 | 1 | 5 | 5 |
| | | Post (13) | 3 | 2 | 2 | 3 | 4 | 4 | 2 | 4 | 5 | 3 | 3 | 0 |
| 8 | 5 | Post (21) | 1 | 0 | 3 | 3 | 1 | 1 | 3 | 4 | 3 | 3 | 2 | 0 |
| 9 | 4 | Pre (20) | — | 1 | 0 | 3 | 1 | 3 | 2 | 3 | 0 | 2 | 2 | 5 |
| 9 | 2 | Post (21) | — | 3 | 4 | 3 | 4 | 4 | 4 | 4 | 4 | 4 | 4 | 4 |
| 9 | 1 | Post (21) | — | 1 | 3 | 2 | 3 | 4 | 4 | 4 | 4 | 5 | 4 | 4 |
| 9 | 0.5 | Post (21) | — | 1 | 3 | 2 | 3 | 3 | 4 | 3 | 2 | 4 | 3 | 3 |
| 13 | 5 | Pre (20) | — | 0 | 0 | 1 | 0 | 0 | 0 | — | 0 | 0 | — | — |
| | | Post (13) | 3 | 1 | 1 | 1 | 0 | 2 | 1 | 4 | 2 | 3 | 3 | 1 |
| 15 | 5 | Pre (20) | 0 | 0 | 1 | 0 | 0 | 0 | 0 | 0 | 0 | 0 | 1 | 0 |
| | | Post (13) | — | 0 | 4 | 2 | 0 | 3 | 3 | 4 | 4 | 4 | 3 | 2 |
| 16 | 2 | Post (21) | — | 2 | 4 | 2 | 4 | 4 | 4 | 4 | 4 | 4 | 4 | 4 |
| 17 | 1 | Post (21) | — | 1 | 3 | 1 | 4 | 4 | 3 | 4 | 4 | 4 | 3 | 2 |
| 23 | 1 | Post | 4 | 4 | 3 | 3 | 4 | 4 | 5 | 5 | 5 | 5 | 3 | 3 |

| Names of test plants | |
|---|---|
| Sb | Sugar beet |
| Rp | Rape |
| Ct | Cotton |
| Sy | Soya Bean |
| Mz | Maize |
| Ww | Winter Wheat |
| Rc | Rice |
| Sn | Senecio vulgaris |
| Ip | Ipomoae purpurea |
| Am | Amaranthus retroflexus |
| Pi | Polygonum aviculare |
| Ca | Chenopodium album |
| Ga | Galium aparine |
| Xa | Xanthium spinosum |
| Ab | Abutilon theophrasti |
| Co | Cassia obtusifolia |
| Av | Avenua fatua |
| Dg | Digitaria sanguinalis |
| Al | Alopecurus myosuroides |
| St | Setaria viridis |
| Ec | Echinochloa crus-galli |
| Sh | Sorghum halepense |
| Ag | Agropyron repens |
| Cn | Cyperus rotundus |

I claim:

1. A phosphonic acid derivative of the formula (I)

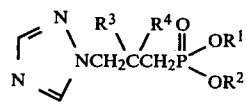

(I)

wherein $R^1$ and $R^2$ each represent a hydrogen atom; a cation; an alkyl radical of 1 to 6 carbon atoms, or an alkenyl or alkynyl radical of 3 to 6 carbon atoms each of which may be substituted with hydroxy, alkoxy of 1 to 6 carbon atoms, halogen or phenyl;

a cyclopentyl or cyclohexyl radical;

or a phenyl radical optionally substituted with hydroxy, alkoxy of 1 to 6 carbon atoms, halogen, or alkyl of 1 to 4 carbon atoms;

$R^3$ may be hydrogen or alkyl of 1 to 3 carbon atoms; $R^4$ may be (a) hydrogen, hydroxy, fluoro, amino, (b) alkoxy of 1 to 6 carbon atoms or alkenyloxy or alkynyloxy of 2 to 6 carbon atom, the last three foregoing radicals being optionally substituted by halogen, alkoxy of 1 to 6 carbon atoms, carboxy, alkoxycarbonyl or phenyl, (c) alkylcarbonyloxy of 2 to 6 carbon atoms optionally substituted by halogen, phosphonomethylamino, or phenyl (d) benzoyloxy optionally substituted by hydroxy, alkoxy of 1 to 6 carbon atoms, halogen, or alkyl of 1 to 4 carbon atoms (e) a mono- or dialkylcarbamoyloxy radical wherein the alkyl group or groups contain from 1 to 6 carbon atoms (f) a benzyloxycarbonyloxy or phenoxycarbonyloxy radical optionally substituted by hydroxy, alkoxy of 1 to 6 carbon atoms, halogen, or alkyl of 1 to 4 carbon atoms (g) alkoxycarbonyloxy of 2 to 6 carbon atoms or $R^3$ and $R^4$ may, together with the carbon atom to which they are attached, form a keto group or an oxime, hydrazone, phenylhydrazone, semi-carbazone, or ketal thereof; or, in the case where neither of $R^1$ and $R^2$ is a cation, an acid addition salt of a phosphonic acid derivative of formula (I).

2. A compound as claimed in claim 1 wherein at least one of $R^1$ and $R^2$ is a cation which is an alkali metal, alkaline earth metal, ammonium, organic ammonium, trialkylsulphonium, trialkylsulphoxonium, phosphonium, or amidinium cation.

3. A compound as claimed in claim 1 wherein $R^3$ is hydrogen and $R^4$ is a hydroxy group.

4. A compound as claimed in claim 1, wherein each of $R^1$ and $R^2$ is a hydrogen atom or a cation, $R^3$ is hydrogen, and $R^4$ is a hydroxy group.

5. A compound according to claim 1 wherein $R^1$, $R^2$ and $R^3$ are hydrogen and $R^4$ is hydroxy.

6. Herbicidal compositions comprising as an active ingredient a compound of formula (I) as defined in claim 1, in admixture with a carrier comprising a solid or liquid diluent, and optionally further comprising a surface-active agent.

7. A method of controlling the growth of unwanted plants, which comprises applying to the plants, or to the locus of the plants a herbicidal amount of a compound of formula (I) as defined in claim 1.

* * * * *